United States Patent
Drake et al.

(10) Patent No.: US 11,117,282 B2
(45) Date of Patent: Sep. 14, 2021

(54) GUIDE CATHETER SLITTER

(71) Applicant: Medtronic, Inc., Minneapolis, MN (US)

(72) Inventors: Ron A. Drake, St. Louis Park, MN (US); Stanten C. Spear, Arden Hills, MN (US); Beth C. Bullemer, Dayton, OH (US); Les Stener, Blaine, MN (US); Gary R. Fiedler, Forest Lake, MN (US); Kendra Yasger, Big Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 262 days.

(21) Appl. No.: 16/017,537

(22) Filed: Jun. 25, 2018

(65) Prior Publication Data

US 2018/0304485 A1    Oct. 25, 2018

Related U.S. Application Data

(63) Continuation of application No. 14/823,133, filed on Aug. 11, 2015, now Pat. No. 10,005,193, which is a
(Continued)

(51) Int. Cl.
*B26D 3/00* (2006.01)
*A61M 25/01* (2006.01)
(Continued)

(52) U.S. Cl.
CPC ............. *B26D 3/001* (2013.01); *A61M 25/01* (2013.01); *A61M 25/0668* (2013.01);
(Continued)

(58) Field of Classification Search
CPC .............. B26D 3/001; A61M 25/0668; A61M 2025/0188; A61M 2025/0675; H02G 1/1217
See application file for complete search history.

(56) References Cited

U.S. PATENT DOCUMENTS 2,018,149 A    10/1935    Randle et al.
3,057,232 A    10/1962    Cornell
(Continued)

FOREIGN PATENT DOCUMENTS

WO    WO 01/02047 A1    1/2001
WO    WO 2006/085119 A1    8/2006
(Continued)

OTHER PUBLICATIONS

International Search Report and Written Opinion for PCT/US2008/074139.
(Continued)

*Primary Examiner* — Emily L Schmidt
*Assistant Examiner* — Leah J Swanson
(74) *Attorney, Agent, or Firm* — Mueting Raasch Group

(57) ABSTRACT

A slitter for slitting a guide catheter has a handle and a blade assembly coupled to the handle. The blade assembly includes a shroud for receiving an elongated body of a medical device and a slitting blade having an exposed cutting edge to slit the guide catheter. The blade assembly includes a user-deflectable portion coupled to the shroud for causing the shroud to flex in response to deflection of the user-deflectable portion. The handle and the blade assembly may be assembled from piece parts in a manufacturing method.

9 Claims, 6 Drawing Sheets

Related U.S. Application Data continuation of application No. 11/844,912, filed on Aug. 24, 2007, now Pat. No. 9,119,940.

(51) Int. Cl.
*A61M 25/06* (2006.01)
*H02G 1/12* (2006.01)

(52) U.S. Cl.
CPC .............. *A61M 2025/0188* (2013.01); *A61M 2025/0675* (2013.01); *H02G 1/1217* (2013.01); *Y10T 29/49826* (2015.01)

(56) References Cited

U.S. PATENT DOCUMENTS

| | | | |
|---|---|---|---|
| 3,518,757 | A | 7/1970 | Grant |
| 3,624,901 | A | 12/1971 | Pettit et al. |
| 3,793,682 | A | 2/1974 | Nelson |
| 3,831,274 | A | 8/1974 | Horrocks |
| 3,898,733 | A | 8/1975 | Cormier |
| 4,373,263 | A * | 2/1983 | Ayers .............. A61B 17/32093 30/294 |
| 4,394,828 | A | 7/1983 | Garbis et al. |
| 4,433,484 | A | 2/1984 | Antisdel et al. |
| 4,631,059 | A | 12/1986 | Wolvek et al. |
| 4,687,469 | A | 8/1987 | Osvpka |
| 4,997,092 | A | 3/1991 | Dupont |
| 4,997,424 | A | 3/1991 | Little |
| 5,188,606 | A | 2/1993 | Maloney et al. |
| 5,261,887 | A | 11/1993 | Walker |
| 5,330,460 | A | 7/1994 | Moss et al. |
| 5,359,690 | A | 10/1994 | Kaizu et al. |
| 5,687,727 | A | 11/1997 | Kraus et al. |
| 5,873,858 | A | 2/1999 | Schafer et al. |
| D433,929 | S | 11/2000 | Petzl |
| 6,148,521 | A | 11/2000 | Eslambolchi et al. |
| 6,159,198 | A | 12/2000 | Gardeski et al. |
| 6,247,235 | B1 | 6/2001 | Lawler |
| 6,277,108 | B1 | 8/2001 | McBroom et al. |
| 6,280,433 | B1 | 8/2001 | McIvor et al. |
| 6,334,253 | B1 | 1/2002 | Cheng |
| 6,368,337 | B1 | 4/2002 | Kieturakis et al. |
| 6,497,681 | B1 | 12/2002 | Brenner |
| 6,544,247 | B1 | 4/2003 | Gardeski et al. |
| 7,029,460 | B2 | 4/2006 | Gardeski et al. |
| 7,264,001 | B2 | 9/2007 | Boutillette et al. |
| 7,338,481 | B2 | 3/2008 | Gardeski et al. |
| D576,279 | S | 9/2008 | Bullemer et al. |
| D576,280 | S | 9/2008 | Bullemer et al. |
| 7,462,167 | B2 | 12/2008 | Kratz et al. |
| D608,003 | S | 1/2010 | Bullemer et al. |
| D608,445 | S | 1/2010 | Bullemer et al. |
| 7,950,155 | B2 | 5/2011 | Goode et al. |
| 8,042,273 | B2 | 10/2011 | Drake et al. |
| 8,074,360 | B2 | 12/2011 | Goode et al. |
| 8,584,364 | B2 | 11/2013 | Goode et al. |
| 9,119,940 | B2 | 9/2015 | Drake et al. |
| 2003/0101596 | A1 | 6/2003 | Deville |
| 2003/0158565 | A1 | 8/2003 | Gardeski et al. |
| 2003/0181935 | A1 | 9/2003 | Gardeski et al. |
| 2005/0182435 | A1 | 8/2005 | Andrews et al. |
| 2006/0167417 | A1 | 7/2006 | Kratz et al. |
| 2007/0079511 | A1 | 4/2007 | Osypka |
| 2007/0175049 | A1 | 8/2007 | Goode et al. |
| 2008/0108972 | A1 | 5/2008 | Andrews et al. |
| 2009/0049698 | A1 | 2/2009 | Drake et al. |
| 2009/0054840 | A1 | 2/2009 | Drake et al. |
| 2009/0071012 | A1 | 3/2009 | Shan et al. |
| 2010/0030154 | A1 | 2/2010 | Duffy |
| 2010/0030161 | A1 | 2/2010 | Duffy |
| 2011/0000089 | A1 | 1/2011 | Goode et al. |
| 2012/0036720 | A1 | 2/2012 | Drake et al. |

FOREIGN PATENT DOCUMENTS

| | | |
|---|---|---|
| WO | WO 2007/089985 A1 | 8/2007 |
| WO | WO 2009/029573 A1 | 3/2009 |
| WO | WO 2010/014419 A1 | 2/2010 |

OTHER PUBLICATIONS

Medtronic Technical Manual for the 6218RED Guide Catheter Slitter, 2002, 16 pgs.

* cited by examiner ns the guide catheter with the other hand, all the
time allowing the lead/catheter position to be stably maintained.

GUIDE CATHETER SLITTER

CROSS REFERENCE TO RELATED APPLICATIONS

This application is a continuation of U.S. patent application Ser. No. 14/823,133, filed on Aug. 11, 2015, which is a continuation of U.S. patent application Ser. No. 11/844,912, filed on Aug. 24, 2007, now issued as U.S. Pat. No. 9,119,940 on Sep. 1, 2015, which are incorporated herein by reference in their entireties.

Reference is made to the following commonly-assigned applications: application Ser. No. 29/283,867 by Bullemer et al.; application Ser. No. 29/283,864 by Bullemer et al.; and application Ser. No. 11/844,932 by Drake et al., the entire contents of each disclosure are incorporated herein by reference.

TECHNICAL FIELD

The invention relates generally to elongated medical device delivery systems and, in particular, to a slitter for slitting a guide catheter during removal from an implanted elongated medical device.

BACKGROUND

Elongated medical devices are often deployed to a targeted internal body location using a guide catheter or introducer. Examples of elongated medical devices include implantable medical electrical leads, such as cardiac pacing and sensing leads, and diagnostic or therapeutic catheters, such as electrophysiological mapping catheters and drug delivery catheters. The guide catheter is typically introduced into a blood vessel and the distal end of the guide catheter is advanced to a desired body site. The elongated medical device is then advanced through the guide catheter to a targeted implant site. While maintaining the elongated medical device in the desired position, the guide catheter is withdrawn over the elongated device body, leaving the device in position for monitoring physiological signals or delivering a therapy, such as an electrical stimulation therapy or a pharmacological or biological agent.

Depending on the targeted location and lead/catheter size, the guide catheter may be made with a relatively small diameter in order to allow advancement into narrow veins or arteries. The elongated medical device often includes a connector assembly or hub at a proximal end of the elongated body that is larger in diameter than the inner diameter of the guide catheter. As such, removal of the guide catheter from the implanted device often requires the use of a "slitter", which is used to slit the guide catheter open as it is withdrawn over the elongated medical device. Because guide catheters and therapy delivery or diagnostic leads and catheters are available in a range of sizes, the slitter may be size specific so that it can be secured to the elongated device body and held in a stable position while the guide catheter is slit and removed. As such, a correctly-sized slitter may be required with a particular lead/catheter system.

Positioning a diagnostic or therapeutic lead/catheter at a desired location can be a time-consuming task requiring considerable skill. Once positioned, a physician must carefully remove the guide catheter without dislodging the lead/catheter from its desired location. If dislodgement occurs, repositioning is required which may involve reinserting the guide catheter. As such, a slitter needs to be easy to handle with one hand while the physician carefully withdraws the guide catheter with the other hand, all the time allowing the lead/catheter position to be stably maintained.

DETAILED DESCRIPTION

Figure 1:
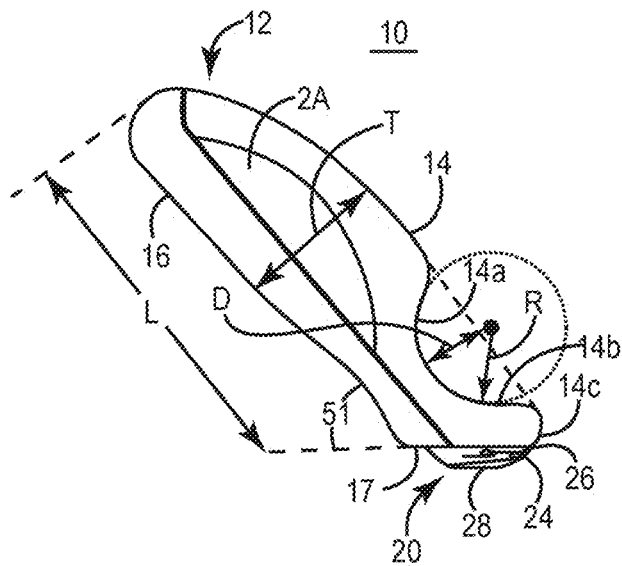
FIG. 1 is a plan view of a slitter for slitting a guide catheter during removal of the guide catheter from an implanted elongated medical device.

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise indicated, drawing elements are not drawn to scale.

FIG. 1 is a plan view of a slitter 10 for slitting a guide catheter during removal of the guide catheter from an implanted elongated medical device. Slitter 10 includes a handle 12 and a blade assembly 20. The blade assembly 20 includes a shroud 28 for receiving the elongated body of a therapeutic or diagnostic medical lead or catheter being deployed to a target location through the guide catheter. As used herein, "guide catheter" refers to any elongated tubular device used in the implantation and delivery of an implantable elongated medical device, such as a medical electrical lead or diagnostic or fluid delivery catheter. As such, the term "guide catheter" as used herein collectively refers to devices also commonly referred to as "introducers" and "delivery catheters".

Handle 12 includes a forward face 14 and a rear face 16 separated by a sidewall 2a and is generally shaped to enable a physician to comfortably and securely grip slitter 10 using one hand. Handle 12 is provided with an ergonomic design intended to fit a range of hand sizes. Handle 12 is formed having an overall size, dimensions and shape to accommodate a whole hand grip. As used herein, a "whole hand" grip refers to a grip or grasp that allows the handle to rest against the palm of the user's hand in contrast to a grip or grasp resulting in contact with only the thumb and one or more fingers. Forward face 14 is shown having a generally arcuate contour and a concave portion 14a and horizontal portion 14b extending from the concave portion for promoting a comfortable grip. The arcuate shape of forward face 14 also makes the intended manner of gripping handle 12 intuitive to a user. Handle 12 is configured to allow a physician to grip slitter 10, using either the left or right hand, by placing a thumb along a user-deflectable portion (not shown in FIG. 1) of shroud 28 that extends along rear face 16 and wrapping his/her fingers around forward face 14, with a forefinger wrapping around concave portion 14a, and resting on horizontal portion 14b (as further shown and described in conjunction with FIG. 10). Concave portion 14a may be formed with a radius R of approximately 1 inch and maximum depth D of at least approximately 0.4 inches to comfortably accommodate a user's forefinger extending along concave portion 14a. Other slitter dimensions, namely an overall length L of rear face 16 and a maximum thickness T of sidewall 2a between forward face 14 and rear face 16 are sized to accommodate a whole hand grip as will be further described below.

As will be described herein, this configuration of handle 12 allows a physician to comfortably grip slitter 10 while retaining an elongated body in shroud 28 by engaging the user-deflectable portion of shroud 28. The concave portion 14a of forward face 14 dissuades the user from gripping handle 12 in an unintended manner that might result in improper forces or torques being applied to the guide catheter and elongated device body. As shown in FIG. 1, rear face 16 may extend upward at an acute angle 51 from a horizontal bottom handle face 17. In various embodiments, rear face 16 may extend at an angle between, but not limited to, about 30 and about 75 degrees, for example 45 degrees, from horizontal bottom face 17.

Handle 12 includes one or more visual alignment aids for indicating an intended alignment of slitter 10 relative to a guide catheter. For example, horizontal bottom face 17 and horizontal portion 14b of forward face 14 provide visual indicators of the intended orientation of the slitter 10 relative to a guide catheter. In particular, the horizontal bottom face 17 and the horizontal portion 14b are intended to be held parallel to the guide catheter in the embodiment shown. Furthermore, the handle 12 and blade assembly 20 may be formed having contrasting colors along bottom face 17 to enhance the visual alignment feature of the horizontal bottom face 17 and encourage parallel alignment of the horizontal bottom face 17 with the guide catheter. In one embodiment, blade assembly 20 is formed from a black material and handle 12 is formed from a white, blue, red, yellow or any other contrasting color. Forward face 14 may further include a leading edge 14c extending perpendicularly between the parallel horizontal portion 14b and horizontal bottom face 17. Leading edge 14c serves as a visual alignment aid in that it will be substantially perpendicular to the guide catheter central axis when the slitter 10 is properly aligned with the guide catheter. These visual alignment aids increase the likelihood of horizontal alignment of handle bottom face 17 with the guide catheter thereby promoting proper alignment of the blade assembly 20 with the guide catheter and proper use of the slitter. Parallel alignment of the horizontal bottom face 17 and the guide catheter will reduce the likelihood of damage or breakage of the guide catheter, the slitter, and the medical device elongated body extending within the guide catheter due to improper pitch, roll or yaw of the slitter relative to the guide catheter.

Handle 12 is coupled to blade assembly 20 along a bottom handle face 17. Blade assembly 20 includes a cutting blade having an exposed, sharpened, forward-facing cutting edge 26 for slitting the guide catheter as it is withdrawn over slitter 10, generally parallel to bottom face 17 and moving in a general direction from forward face 14 to rear face 16, as will be further described herein. Shroud 28 is designed to receive a segment of the body of an elongated medical device to stably maintain the longitudinal position of slitter 10 along the elongated device body during guide catheter removal. Blade assembly 20 further includes a nose piece 24 which becomes positioned between the elongated device body and the inner surface of the guide catheter and acts to guide the guide catheter toward cutting edge 26 as the guide catheter is withdrawn over the slitter 10.

Figure 2A:
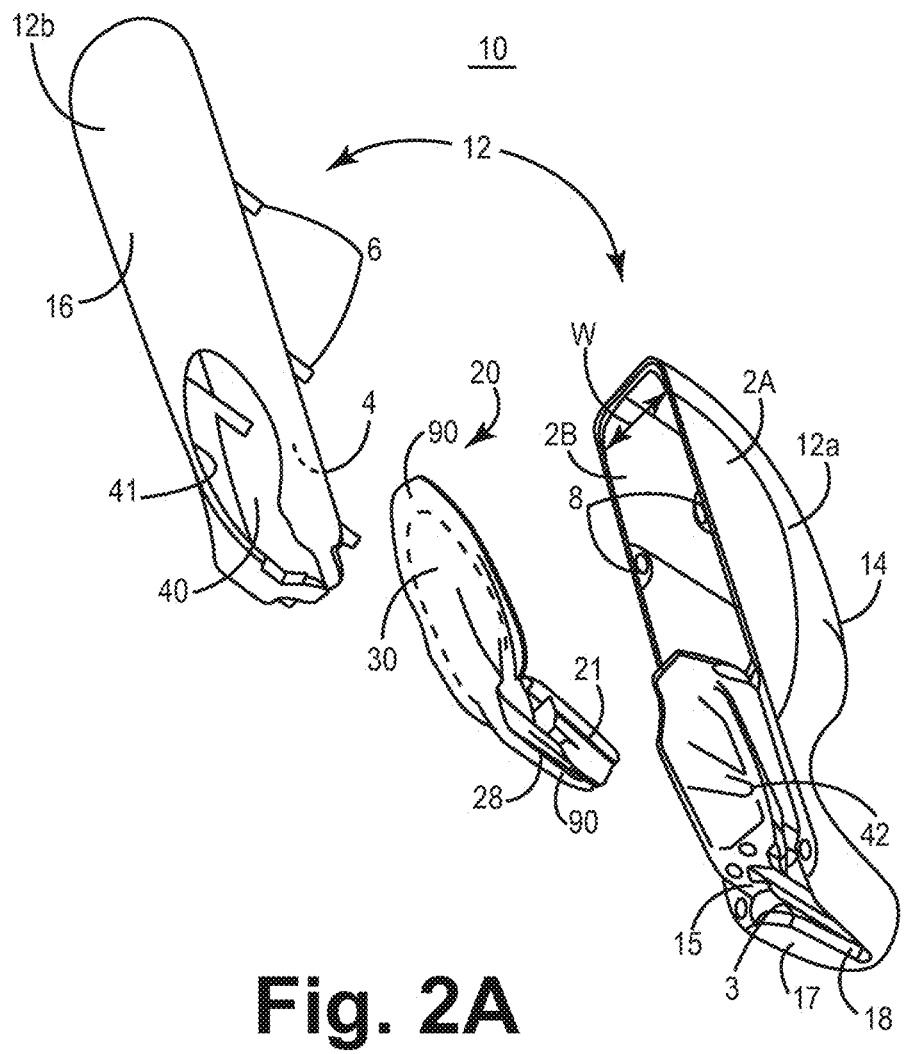
FIG. 2A is an exploded, perspective view of the slitter shown in FIG. 1.

FIG. 2A is an exploded, perspective view of slitter 10. Handle 12 includes a forward portion 12a and a rear portion 12b. Forward portion 12a forms forward face 14 and side walls 2a and 2b, and rear portion 12b forms rear face 16. Forward portion 12a is formed having a slot 18 along bottom face 17 through which shroud 28 of blade assembly 20 extends. Forward portion 12a and blade assembly 20 include interlocking features that become mechanically engaged upon assembling slitter 10. For example, handle forward portion 12a is shown to include a flange 15 for engaging a groove 21 on blade assembly 20. Forward portion 12a further includes a cavity 42 into which the user-deflectable portion 30 of blade assembly 20 can be pressed into by a user. Cavity 42 is generally dome-shaped in the embodiment shown in FIG. 2A such that the outer edges of user-deflectable portion 30 can be supported by the outer edges of cavity 42 while a generally central portion of user-deflectable portion 30 can be deflected into cavity 42 (i.e. in the generally forward direction corresponding to forward face 14 of handle 12).

Rear portion 12b is formed having an edge 41 defining a window 40 through which the user-deflectable portion 30 of blade assembly 20 is exposed after assembling slitter 10. During an assembly process, blade assembly 20 may be first assembled with rear portion 12b, such that user-deflectable portion 30 is aligned with window 40. Next rear portion 12b and forward portion 12a are assembled together. Blade assembly 20 is slid into forward handle portion 12a by engaging groove 21 and flange 15 thereby positioning a forward portion of shroud 28 along slot 18. Rear handle portion 12b may then be assembled with forward handle portion 12a by inserting multiple pegs 6 provided on rear handle portion 12b into respective holes 8 formed in forward portion 12a. Various downward-facing surfaces 90 of blade assembly 20 will variously interface with inner surface 3 of forward handle portion 12a and inner surface 4 of rear handle portion 12b. User-deflectable portion 30 is then exposed through window 40 of handle rear face 16.

Handle portions 12a and 12b may be formed as molded parts fabricated from a rigid polymer material such as, but not limited to, a polycarbonate material, e.g., RTP 301Z available from RTP Company, Winona, Minn. Handle portions 12a and 12b are designed as interlocking components that are press fit together during assembly of slitter 10 and may additionally or alternatively be chemically, thermally, ultrasonically or mechanically coupled using an adhesive, screws, or other joining methods. Handle 12 is made relatively large to provide a secure, comfortable grip, using a "whole hand" grip rather than a grip using only the thumb and, for example, one or two fingers as in past practice. In other words, the overall size of handle 12 allows the handle to rest in the palm of the user's hand while grasping handle 12 with the thumb and up to all four fingers. In making handle 12 relatively large and ergonomically shaped, the assembly of the handle 12 from piece parts, namely portions 12a and 12b, allows handle 12 to be hollow and remain relatively lightweight. Furthermore, forming a hollow handle having cavity 42 allows the user-deflectable portion 30 to be deflected into the handle 12 during slitting. This deflection into the handle facilitates a continuously secure grip and positioning of handle 12 without turning or twisting the slitter 10 relative to the guide catheter.

Handle 12 is sized to accommodate a range of user hand sizes. In particular, dimensions of handle 12 may be selected to accommodate hand sizes ranging from the fifth percentile of female hand sizes to the ninety-fifth percentile of male hand sizes. Hand size measured as the "grip width", across the palm of the hand along the metacarpal heads, ranges from about 2.7 inches for the fifth percentile of female hand sizes to 3.9 inches for the ninety-fifth percentile of male hand sizes. In one embodiment intended to accommodate this range of hand sizes, the handle 12 is provided with an overall length L (shown in FIG. 1) of rear face 16 of about 3.25 inches, a thickness T (shown in FIG. 1) extending between the forward and rear faces 14 and 16 of about 1.1 inches, and a maximum width W extending between side walls 2a and 2b of at least about 0.95 inches. In alternative embodiments intended to accommodate a whole hand grip across hand sizes ranging from the fifth percentile of female hand sizes to the ninety-fifth percentile of male hand sizes the length L may range from about 2.7 inches to about 3.9 inches, the width W may range from about 0.5 inches to about 1.0 inches, and the thickness T may range from about 0.7 inches to about 1.25 inches. The relatively large surface area of handle 12 provides a large area for interfacing with a user's hand, allowing a secure comfortable grip for whole hand maneuvering of the slitter 10, and enhances the tactile feedback during use of the slitter 10.

Figure 2B:
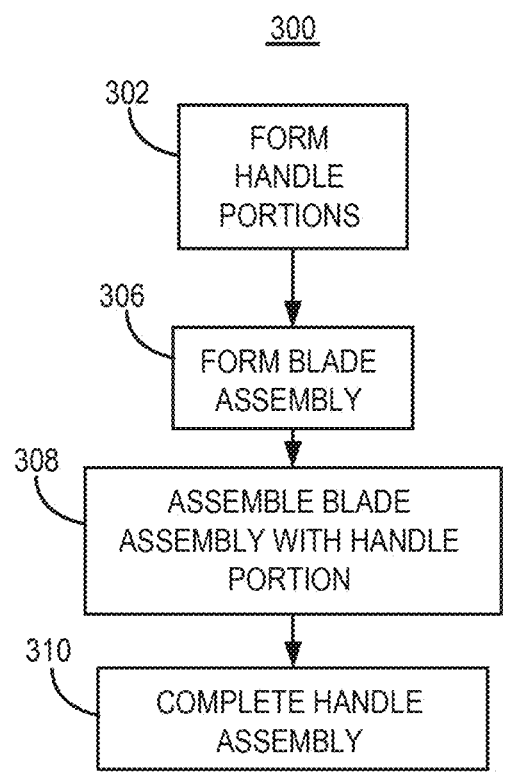
FIG. 2B is a flow chart of a method for manufacturing a slitter according to one embodiment of the invention.

FIG. 2B is a flow chart of a method 300 for manufacturing a slitter according to one embodiment of the invention. Handle portions 12a and 12b are formed as molded and/or machined piece parts at block 302. In one embodiment, the handle is assembled from two portions as shown in FIG. 2A however it is recognized that the handle may be assembled from three or more piece parts. Furthermore it is recognized that while two handle portions as described herein allow the blade assembly to be partially enclosed within and securely retained by the handle during an assembly process, a handle including features described herein could conceivably be fabricated as a single solid or hollow piece with a blade assembly coupled thereto.

The blade assembly 20 is formed at block 306 by overmolding the slitting blade 22, e.g., using an injection molding process. The blade assembly 20 is assembled with a handle portion 12a at block 308. For example, with reference to FIG. 2A, blade assembly 20 may be first assembled with rear portion 12b, such that user-deflectable portion 30 is aligned with window 40. Next rear portion 12b and forward portion 12a are assembled together. User-deflectable portion 30 is aligned with cavity 42 and blade assembly 20 is slid into handle portion 12a by engaging groove 21 with flange 15. At block 310, the handle assembly is completed. In the embodiment shown in FIG. 2A, opposing handle portions 12a and 12b are assembled by mating interlocking features 6 and 8. The blade assembly 20 is securely held by the assembled handle 12.

Figure 3:
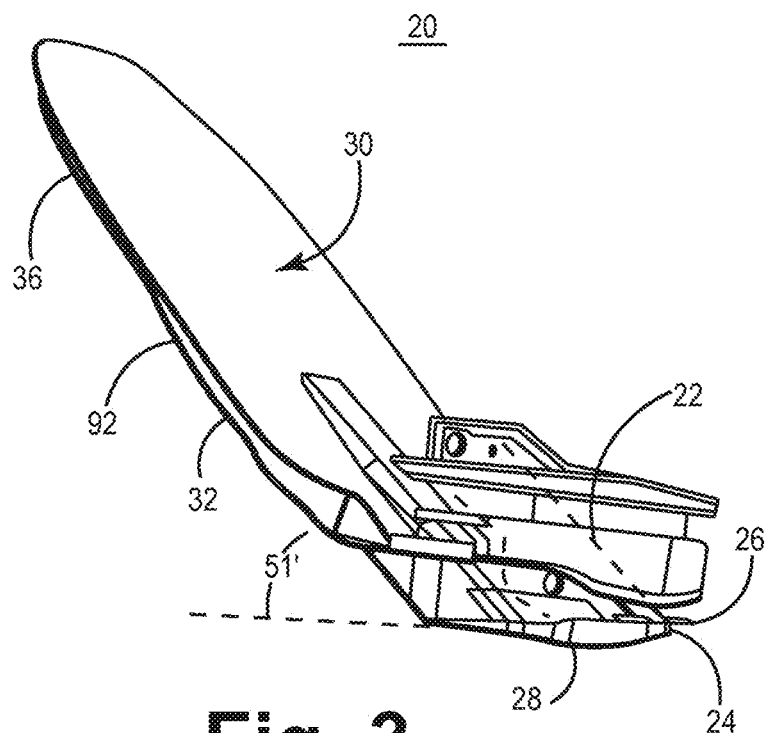
FIG. 3 is a perspective view of a blade assembly included in a slitter according to one embodiment of the invention.

FIG. 3 is a perspective view of blade assembly 20. Blade assembly 20 is formed by overmolding a cutting blade 22, indicated by dashed line, to form shroud 28 with user-deflectable portion 30. User-deflectable portion 30 is formed having a raised portion 32 with an outer edge 92 and a substantially flat portion 36 in one embodiment. Blade assembly 20 may be formed as a molded component formed from, but not limited to, a nylon resin such as Zytel 70G33L available from DuPont, Wilmington, Del. Polymers selected for forming blade assembly 20 are polymers having a generally high tensile strength, e.g., greater than 20,000 psi at room temperature, and a high flex modulus, e.g. greater than 1,200 kpsi, that can be formed very thin to allow flexion of shroud 28 and user-deflectable portion 30. Another example of a suitable polymer material for forming blade assembly is a polypropylene material. In some embodiments, resilient or elastic polymers may be selected as long as deflection of user-deflectable portion 30 formed from such polymers can cause flexion of shroud 28 as will be described herein. The flexibility of shroud 28 and user-deflectable portion 30 can be controlled by controlling the thickness of the material. Areas having greater thickness will be less flexible but provide more efficient transfer of the force applied to user-deflectable portion 30 to shroud 28 to thereby cause deflection of shroud 28 around an elongated device body as will be described in detail below.

The cutting blade 22 mounted in blade assembly 20 is formed, for example, from stainless steel having a beveled edge to form a sharp cutting edge 26. Cutting blade 22 may be formed from other durable metals, coated metals, ceramic materials, cermets, or rigid polymer materials. Blade 22 may include one or more features, e.g., cut-outs, flanges, strips or wires, for enhancing the mechanical engagement between blade 22 and the material used to form blade assembly 20 as generally described in the incorporated co-pending U.S. patent application Ser. No. 11/844,932.

Nose piece 24 extends forward from cutting edge 26 to direct the wall of a guide catheter against cutting edge 26. Nose piece 24 may be provided with relatively small dimensions compared to nose pieces provided on slitters in past practice and may generally correspond to embodiments disclosed in co-pending U.S. patent application Ser. No. 11/844,932. For example, in one embodiment, nose piece 24 is provided having a generally triangular cross-section with a height and width of less than 0.035 inches and extends forward a maximum distance of less than 0.035 inches from cutting edge 26. The small dimensions of nose 24 reduce the likelihood of the nose piece 24 breaking off or separating from blade 22 and reduce the likelihood of nose piece 24 from causing damage to an elongated device body, when the slitter bottom face 17 is held at a downward angle, or in a "nose down" position, toward a guide catheter outer surface, rather than substantially parallel and level with a guide catheter outer surface. The small dimensions and generally triangular shape of nose 24 allow the catheter to still make contact with cutting edge 26 even when the slitter is held in a "nose down" position thereby promoting smooth cutting of the guide catheter wall over cutting edge 26 and reducing the likelihood of ripping or breaking of the guide catheter.

In some embodiments, the blade assembly 20 may be formed of two different materials. A forward portion of the blade assembly that includes nose piece 24 may be formed from a more rigid polymer, such as a nylon resin, and a rear portion of the blade assembly that includes shroud 28 and user-deflectable portion 30 may be formed from a less rigid polymer, for example a polypropylene material, to allow easier deflection of user-deflectable portion 30 and shroud 28 while providing a durable nose piece 24. A blade assembly formed of two different materials in a two-step manufacturing method to achieve different material properties along a forward and back portion of the blade assembly 20 is generally disclosed in the incorporated co-pending application Ser. No. 11/844,932.

Figure 4:
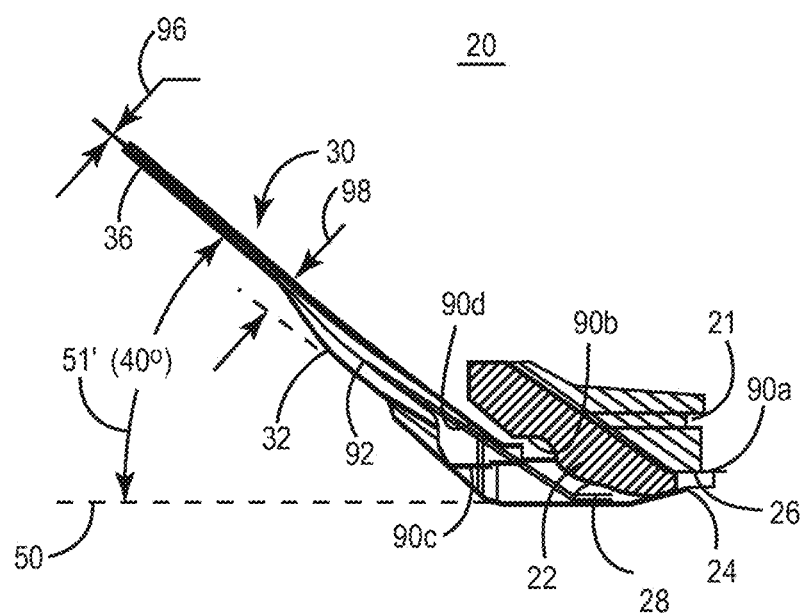
FIG. 4 is a side sectional view of the blade assembly shown in FIG. 3.

FIG. 4 is a side sectional view of blade assembly 20. User deflectable portion 30 is a thin member formed as a continuous component with shroud 28. User-deflectable portion 30 extends upward at an angle 51', for example an angle between, but not limited to, about 30 to about 75 degrees from a central axis 50 of shroud 28. Angle 51' approximately matches angle 51 between handle rear face 16 and handle bottom face 17 shown in FIG. 1 such that user-deflectable portion 30 extends along the window 40 of rear face 16 when assembled with handle 12. Angles 51' and 51 do not need to match exactly, however. For example, in one embodiment, angle 51' is 40 degrees and angle 51 is 45 degrees.

User-deflectable portion 30 is formed very thin, having a thickness 96 of less than, for example, 0.02 inches, to allow a generally rigid polymer used to form blade assembly 20 to flex in a generally forward direction upon manually applying pressure to user-deflectable portion 30. Raised portion 32 is formed having a thickness 98 greater than the thickness 96 of flat portion 36. In one embodiment, flat portion 36 is formed having a thickness 96 of approximately 0.012 to 0.014 inches. Raised portion may have a thickness 98 of approximately 0.05 to 0.2 inches. The thickness of user-deflectable portion 30 is a design selection that takes into account the material used to form user-deflectable portion 30 and shroud 28 and the amount of pressure required to deflect user-deflectable portion 30 a distance into handle 12 (not shown in FIG. 4) to thereby cause a desired flexion of shroud 28 around an elongated device body (as will be described and shown below in conjunction with FIG. 7). In one embodiment, user-deflectable portion 30 and shroud 28 are formed from Zytel 70G33L having a thickness of approximately 0.013 inches along user-deflectable flat portion 36 and approximately 0.10 inches along raised portion 32 to allow manual deflection of user-deflectable portion 30 of approximately 0.05 to 0.1 inches causing an inward flexion of shroud 28 of a similar distance.

In alternative embodiments, user deflectable portion 30 and shroud 28 may be formed of two different materials, either in a two-step molding process or as separate piece parts that become coupled together during an assembly process. Different materials can be selected having the properties needed to tailor the desired mechanical properties of each of portion 30 and shroud 28. It is further recognized that in some embodiments, a user-deflectable portion may include a spring mechanism or an elastic element to return the user-deflectable portion from a deflected position to a normal position.

Cutting blade 22 is shown extending through blade assembly 20 with cutting edge 26 exposed just proximal from nose 24. Groove 21 is provided for engaging a flange included in handle 12 as described previously. Multiple downward-facing faces 90a through 90d of blade assembly 20 interface with an inner surface of handle 12, along bottom face 17 or rear face 16, some of which downward-facing faces 90a through 90d may be partially exposed along bottom face 17 and rear face 16.

Figure 5:
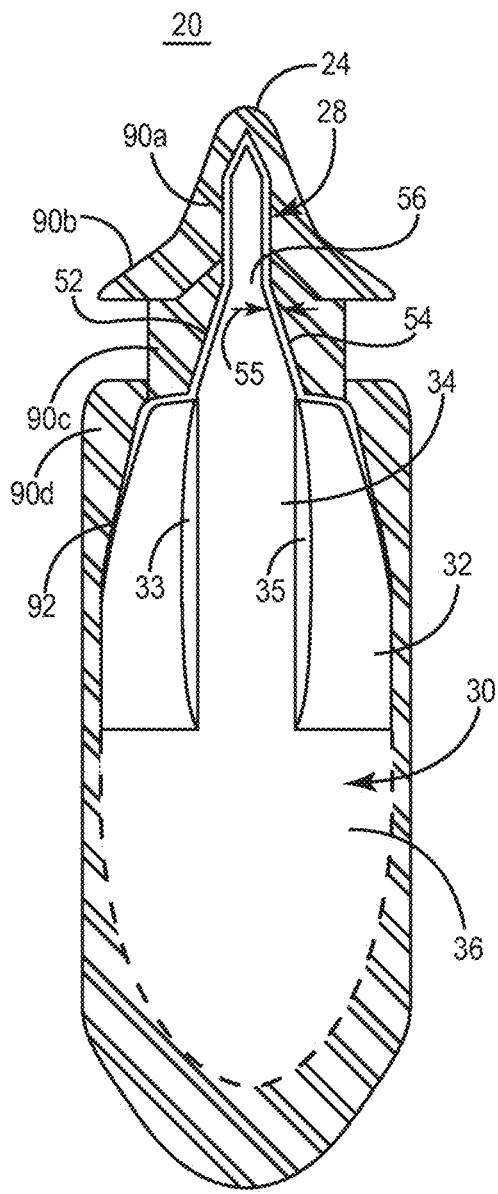
FIG. 5 is a rear, plan view of the blade assembly shown in FIG. 3.

FIG. 5 is a rear, plan view of blade assembly 20. Shroud 28 extends forward from user deflectable portion 30 at an angle 51' as was shown in FIG. 4, and can therefore be seen in this rear view. Shroud 28 begins proximate nose piece 24 and includes opposing flanges 52 and 54 forming a groove 56 therebetween for receiving an elongated device body. Flanges 52 and 54 are formed very thin to promote flexion of flanges 52 and 54 in response to deflection of user-deflectable portion 30. For example, each flange 52 and 54 may be formed having a thickness 55 of less than 0.02 inches. In one embodiment, flanges 52 and 54 formed from Zytel 70G33L have a thickness of approximately 0.010 to 0.012 inches.

User-deflectable portion 30 includes raised portion 32 formed with a groove 34 in communication with shroud groove 56 formed by flanges 52 and 54. Raised portion 32 having edge 92 is provided having a greater thickness than flat portion 36 as described above to facilitate formation of side walls 33 and 35 forming groove 34. An elongated device body extending through shroud 28 can extend further through groove 34. Raised portion 32 slopes down to flat portion 36, as generally shown in the side view FIG. 4. A clinician using slitter 10 can apply pressure against user-deflectable portion 30, thereby causing forward deflection of user-deflectable portion 30 (toward handle forward face, into the paper in the view of FIG. 5). Flanges 52 and 54 flex inward, toward each other, in response to deflection of user-deflectable portion 30. Inward flexion of flanges 52 and 54 retains an elongated device body within shroud 28 and minimizes the potential for buckling of the elongated body.

Figure 6:
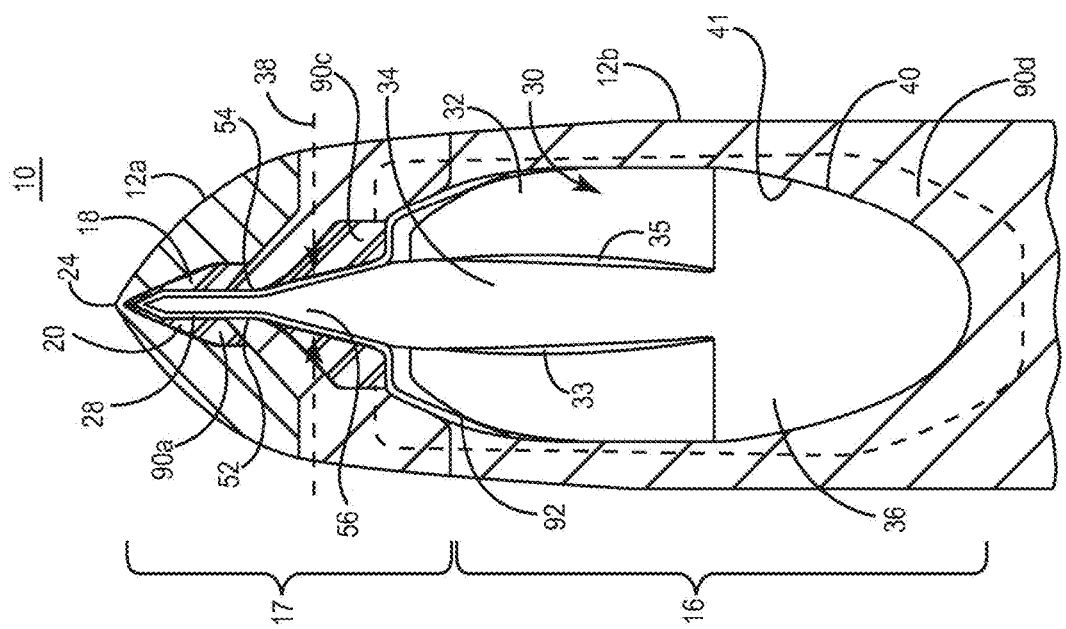
FIG. 6 is a rear, plan view of a slitter according to one embodiment of the invention.

Downward-facing faces 90a, 90b, 90c, and 90d are configured at different elevations, as seen in the side view of FIG. 4, for interfacing with inner surfaces of handle 12. As shown in FIG. 6, portions of downward-facing faces 90a through 90d may be exposed along bottom handle face 17 and rear face 16.

FIG. 6 is a plan view of rear face 16 of slitter 10 showing shroud 28 and user-deflectable portion 30 in a normal position. Bottom face 17 can be seen in this view, extending forward at an angle 51 from rear face 16 as shown in FIG. 1. Forward handle portion 12a includes slot 18 through which shroud 28 extends. Downward-facing surface 90a of blade assembly 20 may be partially exposed through slot 18.

Downward-facing surface 90b is not shown in FIG. 6 as it interfaces with an inner surface of the bottom handle face 17 of rear handle portion 12b and is substantially unexposed. Downward-facing surface 90c is partially exposed along a portion of window 40 formed by edge 41 of rear handle portion 12b. Downward-facing surface 90d, indicated by dashed line, interfaces with an inner surface of rear handle portion 12b with the portion exposed through window 40 forming user-deflectable portion 30. Thus, through the multiple interfacing surfaces 90a through 90d with inner surfaces of handle portions 12a and 12b, blade assembly 20 is securely and mechanically retained within the assembled handle 12.

Upon depressing user-deflectable portion 30 to cause forward deflection of portion 30 (into the paper in the view shown and generally toward slitter forward face 14), side walls 33 and 35 will flex inward, effectively narrowing groove 34 of raised portion 32. This inward flexion of walls 33 and 35 is transferred to flanges 52 and 54 of shroud 28 causing inward flexion, generally in the direction indicated by arrows 38, of flanges 52 and 54.

Deflection of user-deflectable portion 30 can cause separation of outer edge 92 of raised portion 32 from window edge 41. As a result, a greater portion of downward-facing surface 90d will be exposed through window 40. A portion of downward-facing surface 90d, however, remains in contact with an inner surface of rear handle portion 12b to stably retain user-deflectable portion 30 within handle 12.

Figure 7:
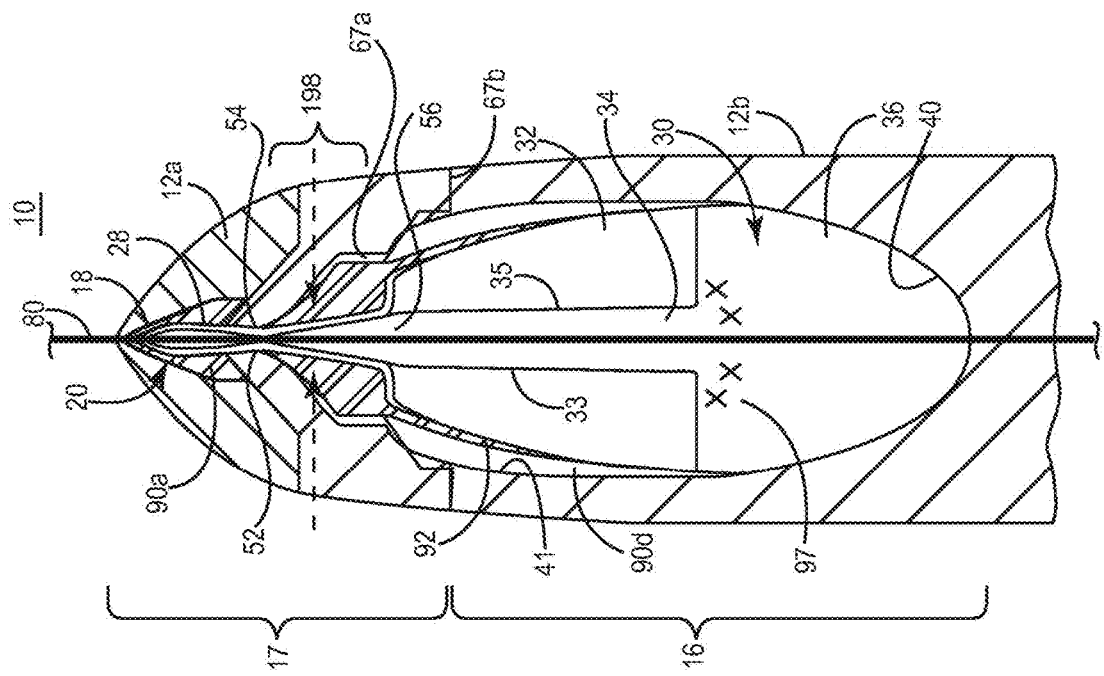
FIG. 7 is a plan view of the slitter rear face shown in FIG. 5 during depression of user-deflectable portion.

FIG. 7 is a plan view of rear face 16 of slitter 10 during inward deflection of user-deflectable portion 30. An elongated device body 80 is shown extending through shroud 28 and groove 34 of user-deflectable portion 30. In response to forward deflection of user-deflectable portion 30, side walls 33 and 35 of raised portion 32 flex inward, narrowing groove 34, and flanges 52 and 54 flex inward around the elongated device body 80, thereby retaining the device body 80 within shroud groove 56. Deflection of flanges 52 and 54 can occur along a majority of the length of shroud 28. Deflection of flanges 52 and 54 will tend to be most significant along a proximal portion 198 of shroud 28, which is most proximate user-deflectable portion 30.

Pressure may be applied by a user anywhere along user-deflectable portion 30 to cause forward deflection of portion 30 and resulting inward flexion of flanges 52 and 54. In one embodiment, pressure applied along an area 97, generally indicated by cross-hatching, of flat portion 36, immediately adjacent raised portion 32, causes the greatest response of flanges 52 and 54 with the least amount of exerted pressure. Raised portion 32 helps to reduce slippage of the user's thumb along user-deflectable portion 30. A digit of a user's hand (not shown), typically the thumb, used to apply pressure along user-deflectable portion 30 will also act to hold elongated body 80 against user-deflectable portion 30, helping to maintain a stable longitudinal location of slitter 10 along elongated body 80. The user can hold the elongated device body 80 between his/her thumb and the user-deflectable portion 30 for tactile assurance that the elongated body 80 is securely held and not being shifted or dislodged. Stops 67a and 67b may be formed on the distal portion (corresponding to a direction toward shroud 28) of user deflectable portion 30 and rear face 16, respectively. When a user positions a thumb flat along user-deflectable portion 30, stops 67a and 67b act to stop forward slippage of the thumb.

Slitter 10 accommodates a range of elongated body diameters, for example, but not limited to, 4 to 6 French. Grooves 56 and 34 may be formed relatively wide, for example 0.1 inches or more, to accommodate larger diameter elongated device bodies. However, slitter 10 can be used effectively with relatively large, e.g. 6 French or larger, as well as small diameter elongated bodies, e.g. 4 French or smaller, since flanges 52 and 54 can be flexed inward around the elongated body to thereby retain the body within grooves 56 and 34.

While one particular configuration of a user-deflectable portion coupled to a shroud to thereby allow flexion of the shroud in response to deflection of the user-deflectable portion is shown, it is recognized that numerous variations of a user-deflectable portion extending from a shroud to cause flexion thereof may be conceived. For example, in other embodiments, a shroud may include a single flange with a user-deflectable portion positioned adjacent the single flange to cause flexion of the flange around an elongated device body. In still other embodiments, the shroud may be configured to flex in response to squeezing a user-deflectable portion positioned along major sides of a generally flat handle.

In the configuration shown in FIGS. 6 and 7, the shroud is in a normally "open" position corresponding to receiving or releasing an elongated device body. The shroud flexes in response to deflection of the user-deflectable portion to a "closed" position corresponding to retaining an elongated device body within the shroud. It is further recognized that, in other embodiments, deflection of a user-deflectable portion may cause a shroud to flex from a normally "closed" position corresponding to retaining an elongated device body to a normally "open" position corresponding to releasing an elongated device body. For example, a user-deflectable portion, positioned along a forward face of the slitter, may be pushed "backward" against an inner surface of the shroud to cause the shroud to flex open to receive or release an elongated body. Release of the user-deflectable portion would allow the shroud to return to a normally closed position to retain an elongated body.

Figure 8:
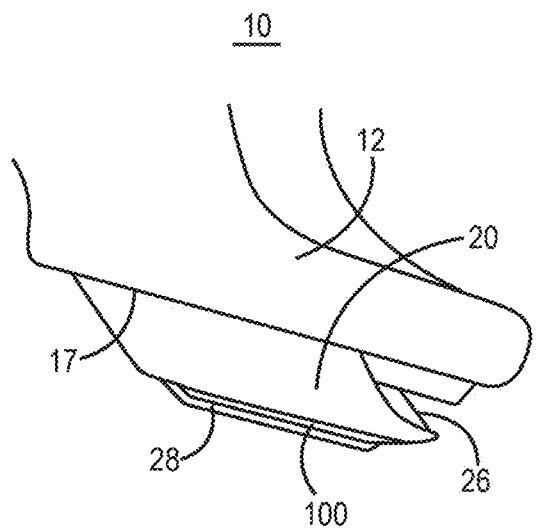
FIG. 8 is a perspective view of a blade assembly including a catheter guide rail.

FIG. 8 is an enlarged, perspective view of a forward portion of slitter 10 according to one embodiment. Blade assembly 20 extends along bottom face 17 of handle 12. A guide rail 100 is shown extending along a majority of the length of shroud 28. As a guide catheter is withdrawn over an elongated device body and slit by cutting edge 26, the cut edges of the guide catheter pass along guide rail 100. In this way, the elongated device body extending through shroud 28 is protected from the cut wall of the guide catheter. The guide rail 100, which may extend along the shroud 28 for about 0.5 inches or more, maintains engagement between the slitter 10 and the guide catheter, reducing the tendency of the guide catheter to fall away from slitter 10 during the slitting procedure.

Figure 9:
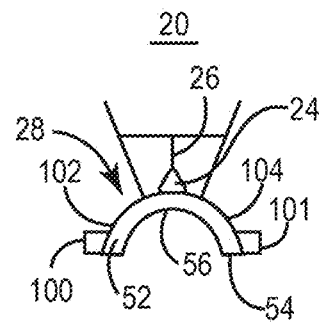
FIG. 9 is a front view of a forward portion of a slitter including a catheter guide rail.

FIG. 9 is a front view of blade assembly 20 showing nose piece 24, just below and protruding forward from cutting edge 26. Flanges 52 and 54 of shroud 28 have inner surfaces forming groove 56. Catheter guide rails 100 and 101 are shown extending laterally outward from outer surfaces 102 and 104 of flanges 52 and 54, respectively. Guide rails 100 and 101 direct the cut walls of the guide catheter being slit by cutting edge 26 over the slitter and help to maintain a proper position of the guide catheter relative to the cutting edge 26. The guide catheter engagement with the slitter is better maintained by the guide rails, which act to prevent the catheter from falling off the slitter. The guide rails also provide resistance against angling the slitter in a "nose-down" position and thereby promote maintenance of a substantially parallel orientation between the slitter lower edge 17 (not seen in FIG. 9) and the guide catheter outer surface.

The guide catheter cut edges may apply pressure along the outer surfaces 102 and 104 of flanges 52 and 54 thereby causing inward flexion of flanges 52 and 54 around an elongated device body extending through shroud 28. This additional pressure applied to the outer surfaces 102 and 104 by the cut guide catheter walls may therefore contribute to stably retaining the elongated device body within shroud 28.

Figure 10:
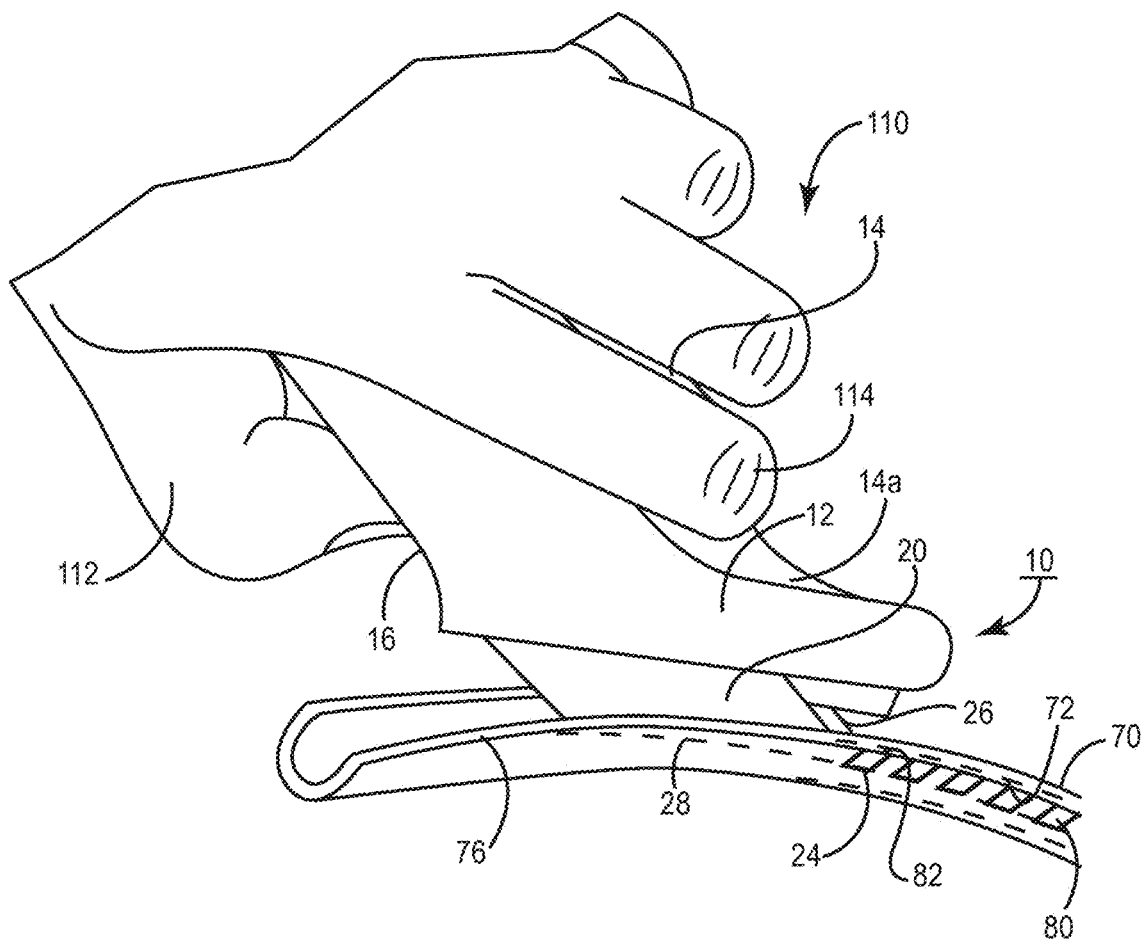
FIG. 10 is a perspective view of a slitter positioned along an elongated device body as a guide catheter is advanced over the slitter.

FIG. 10 is a perspective view of slitter 10 positioned along an elongated device body 80 as a guide catheter 70 is advanced over the slitter 10. A user 110 grasps handle 12 by placing a thumb 112 over user-deflectable portion 30 (not shown) along rear face 16 and wrapping his/her fingers around forward face 14, extending a forefinger 114 along concave portion 14a. The user 110 deflects the user-deflectable portion 30 (not seen in FIG. 10) using thumb 112, into cavity 42 (shown in FIG. 2A), generally in a forward direction toward forward face 14. This deflection causes flexion of shroud 28 around the device body 80, thereby retaining the device body 80 within shroud 28 as described previously.

Guide catheter 70 includes an open lumen, formed by inner surface 72, through which the elongated device body 80 extends. Nose piece 24 is positioned between the inner surface 72 of guide catheter 70 and an outer surface 82 of elongated body 80. Guide catheter wall 76 is then slit open by cutting edge 26 as guide catheter 70 is withdrawn over elongated body 80 and passed along blade assembly 20.

Thus, a slitter for use in removing a guide catheter from an elongated medical device body has been presented in the foregoing description with reference to specific embodiments. It is appreciated that various modifications to the referenced embodiments may be made without departing from the scope of the invention as set forth in the following claims.

The invention claimed is:

1. A guide catheter slitter comprising:
   a blade assembly comprising:
      a shroud extending along a central axis to receive an elongated body of a medical device, and
      a slitting blade comprising an exposed cutting edge; and
   a handle coupled to the blade assembly defining:
      a bottom face proximate the blade assembly, and
      a rear face extending from the bottom face at an acute angle between 30 degrees and 75 degrees defined between the rear face and the central axis, the rear face comprising a user-deflectable thumb portion that deflects into a cavity in the handle for placement of a user's thumb when the user grasps the handle.

2. The slitter of claim 1 wherein the handle further defines an arcuate forward face comprising a concave portion, the forward, rear, and bottom faces configured to accommodate a whole hand grip.

3. The slitter of claim 1 wherein the slitting blade lies in a blade plane and the rear face extends substantially along a rear face plane, wherein the blade plane and the rear face plane are perpendicular to each other.

4. The slitter of claim 1 wherein the shroud comprises:
   a first flange; and
   a second flange opposing the first flange, wherein the first and second flange define a groove extending therebetween to receive the elongated body.

5. The slitter of claim 4 wherein the thumb portion defines a groove to receive the elongated body being in communication with the groove of the shroud.

6. The handle of claim 1 wherein the thumb portion comprises a raised portion to reduce slippage of the user's thumb, the raised portion defining a groove to receive the elongated body.

7. The slitter of claim 1 wherein the blade assembly further comprises a nose piece extending forward from the cutting edge to direct the guide catheter toward the cutting edge.

8. The slitter of claim 1 further comprising a parallel visual alignment aid indicating an intended parallel alignment between the slitter and the guide catheter.

9. A guide catheter slitter comprising:
   a blade assembly comprising:
      a shroud extending along a central axis to receive an elongated body of a medical device, and
      a slitting blade comprising an exposed cutting edge; and
   a handle coupled to the blade assembly defining:
      a bottom face proximate the blade assembly,
      a rear face extending from the bottom face, the rear face comprising a user-deflectable thumb portion that deflects into a cavity in the handle when the user grasps the handle,
      an arcuate forward face opposite the rear face, and
      a pair of sidewalls extending between the rear face and the arcuate forward face, at least one sidewall of the pair of sidewalls and the rear face defining a palm rest to receive the user's palm when the user grasps the handle.

* * * * *